(12) United States Patent
Fowler et al.

(10) Patent No.: US 7,647,186 B2
(45) Date of Patent: Jan. 12, 2010

(54) OLIGONUCLEOTIDE ORDERING SYSTEM

(75) Inventors: Craig A. Fowler, Temecula, CA (US);
Vinod C. Mehta, San Diego, CA (US);
Thomas L. Rosso, Del Mar, CA (US)

(73) Assignee: Illumina, Inc., San Diego, CA (US)

( * ) Notice: Subject to any disclaimer, the term of this patent is extended or adjusted under 35 U.S.C. 154(b) by 614 days.

(21) Appl. No.: 11/184,215

(22) Filed: Jul. 15, 2005

(65) Prior Publication Data
US 2006/0122790 A1 Jun. 8, 2006

Related U.S. Application Data

(60) Provisional application No. 60/634,164, filed on Dec. 7, 2004.

(51) Int. Cl.
*G06F 7/00* (2006.01)

(52) U.S. Cl. .............................. 702/19; 702/20; 703/11; 703/13; 707/102; 536/24.5

(58) Field of Classification Search ........................ None
See application file for complete search history.

(56) References Cited

U.S. PATENT DOCUMENTS

| | | | |
|---|---|---|---|
| 5,143,854 A | 9/1992 | Pirrung et al. | |
| 5,242,974 A | 9/1993 | Holmes | |
| 5,252,743 A | 10/1993 | Barrett et al. | |
| 5,324,633 A | 6/1994 | Fodor et al. | |
| 5,384,261 A | 1/1995 | Winkler et al. | |
| 5,405,783 A | 4/1995 | Pirrung et al. | |
| 5,424,186 A | 6/1995 | Fodor et al. | |
| 5,445,934 A | 8/1995 | Fodor et al. | |
| 5,451,683 A | 9/1995 | Barrett et al. | |
| 5,482,867 A | 1/1996 | Barrett et al. | |
| 5,491,074 A | 2/1996 | Aldwin et al. | |
| 5,527,681 A | 6/1996 | Holmes | |
| 5,550,215 A | 8/1996 | Holmes | |
| 5,571,639 A | 11/1996 | Hubbell et al. | |
| 5,578,832 A | 11/1996 | Trulson et al. | |
| 5,593,839 A | 1/1997 | Hubbell et al. | |
| 5,599,695 A | 2/1997 | Pease et al. | |
| 5,624,711 A | 4/1997 | Sundberg et al. | |
| 5,631,734 A | 5/1997 | Stern et al. | |
| 5,744,305 A | 4/1998 | Fodor et al. | |
| 5,795,716 A | 8/1998 | Chee | |
| 5,831,070 A | 11/1998 | Pease et al. | |
| 5,837,832 A | 11/1998 | Chee et al. | |
| 5,856,101 A | 1/1999 | Hubbell et al. | |
| 5,858,659 A | 1/1999 | Sapolsky et al. | |
| 5,936,324 A | 8/1999 | Montagu | |
| 5,968,740 A | 10/1999 | Fodor et al. | |
| 5,974,164 A | 10/1999 | Chee | |
| 5,981,185 A | 11/1999 | Matson et al. | |
| 5,981,956 A | 11/1999 | Stern | |
| 6,022,693 A | 2/2000 | Baumgartner | |
| 6,023,540 A | 2/2000 | Walt et al. | |
| 6,025,601 A | 2/2000 | Trulson et al. | |
| 6,033,860 A | 3/2000 | Lockhart et al. | |
| 6,040,193 A | 3/2000 | Winkler et al. | |
| 6,083,697 A | 7/2000 | Beecher et al. | |
| 6,090,555 A | 7/2000 | Fiekowsky et al. | |
| 6,136,269 A | 10/2000 | Winkler et al. | |
| 6,200,737 B1 | 3/2001 | Walt et al. | |
| 6,269,846 B1 | 8/2001 | Overbeck et al. | |
| 6,282,550 B1 * | 8/2001 | Venkatesan et al. | ...... 707/104.1 |
| 6,291,183 B1 | 9/2001 | Pirrung et al. | |
| 6,309,831 B1 | 10/2001 | Goldberg et al. | |
| 6,327,410 B1 | 12/2001 | Walt et al. | |
| 6,355,431 B1 | 3/2002 | Chee et al. | |
| 6,428,752 B1 | 8/2002 | Montagu | |
| 6,429,027 B1 | 8/2002 | Chee et al. | |
| 6,692,972 B1 * | 2/2004 | Yershov et al. | .............. 436/180 |
| 2002/0102578 A1 | 8/2002 | Dickinson et al. | |
| 2003/0040870 A1 * | 2/2003 | Anderson et al. | ............. 702/20 |

FOREIGN PATENT DOCUMENTS

| | | |
|---|---|---|
| WO | WO 98/40726 | 9/1998 |
| WO | WO 98/50782 | 11/1998 |
| WO | WO 99/00730 | 1/1999 |
| WO | WO 99/36760 | 7/1999 |
| WO | WO 00/58516 | 10/2000 |
| WO | WO 00/63437 | 10/2000 |
| WO | WO 01/04285 | 1/2001 |

OTHER PUBLICATIONS

U.S. Appl. No. 09/536,841, filed Mar. 27, 2000, Fan.

* cited by examiner

*Primary Examiner*—Mary K Zeman
(74) *Attorney, Agent, or Firm*—Knobbe, Martens, Olson & Bear LLP

(57) ABSTRACT

A system is described for ordering oligonucleotides through a network, such as the Internet. The system provides a mechanism for validating the data provided by a customer, and then displaying graphical images to represent any data that has errors. The system can also pool multiple oligonucleotide samples together by providing graphical images representing oligonucleotide containers, and allowing the customer to select the proper containers to pool.

17 Claims, 9 Drawing Sheets

FIG. 6

OLIGONUCLEOTIDE ORDERING SYSTEM

CROSS REFERENCE TO RELATED APPLICATIONS

This application claims the benefit of U.S. Provisional Application Ser. No. 60/634,164 filed Dec. 7, 2004 and entitled "Oligonucleotide Ordering System" the entirety of which is hereby incorporated by reference.

FIELD OF THE INVENTION

This invention relates to a system for ordering oligonucleotides. More specifically, the invention relates to an on-line ordering system for ordering oligonucleotides through a computer network.

BACKGROUND OF THE INVENTION

Description of the Related Art

Many product ordering systems are available on the Internet. Companies such as Amazon®, Dell®, Microsoft® and many others sell a variety of products through the Internet. However, the process of ordering biological reagents that are used for specific experimental procedures can be daunting. For example, many biological products require specific customization that has been difficult to implement through an Internet ordering system.

One such biological product is an oligonucleotide, essentially a fragment of DNA that is used in a variety of experimental procedures. Although some companies provide systems for ordering oligonucleotides on-line, the ability to customize such orders and the efficiency of the ordering systems is limited. Thus, what is needed in the art is an efficient mechanism for ordering custom oligonucleotides through the Internet.

SUMMARY OF THE INVENTION

One embodiment of the invention is a system for ordering oligonucleotides, that includes: a database configured to receive a parameter defining a type of container for storing the oligonucleotides; a server comprising a storage configured to receive a customer data file comprising oligonucleotide sequence data; a first module configured to check the parameter and the oligonucleotide sequence data for errors; and a second module configured to display a graphic representing the type of container, wherein the graphic indicates whether the oligonucleotide sequence data has at least one error.

Another embodiment of the invention is an online system for creating an order for a mixture of different oligonucleotides. This embodiment includes: a first module configured to present graphics representing a first container and a second container for holding oligonucleotides, where the graphics are selectable by a customer; a storage for storing the identity of graphics that are selected by the customer; and a second module configured to identify the containers corresponding to the graphics selected by the customer and creating an order for a container comprising a mixture of oligonucleotides from the selected containers.

Still another embodiment of the invention is a method in a computer for ordering oligonucleotides online that includes: receiving a parameter defining a type of container for storing oligonucleotides; storing a customer data file comprising oligonucleotide sequence data; verifying the parameter and the oligonucleotide sequence data for errors; and displaying a graphic representing the type of container, wherein the graphic indicates whether the oligonucleotide sequence data has at least one error.

One other embodiment of the invention is a method for creating an order for a mixture of different oligonucleotides. This embodiment includes: presenting graphics representing a first container and a second container for holding oligonucleotides, where the graphics are selectable by a customer; storing the identity of graphics that are selected by the customer; identifying the containers corresponding to the graphics selected by the customer; and creating an order for a container comprising a mixture of oligonucleotides from the selected containers.

BRIEF DESCRIPTION OF THE DRAWINGS

FIG. 6 is a screenshot of container graphics illustrating a valid oligonucleotide order.

DETAILED DESCRIPTION OF THE PREFERRED EMBODIMENTS

Figure 1:
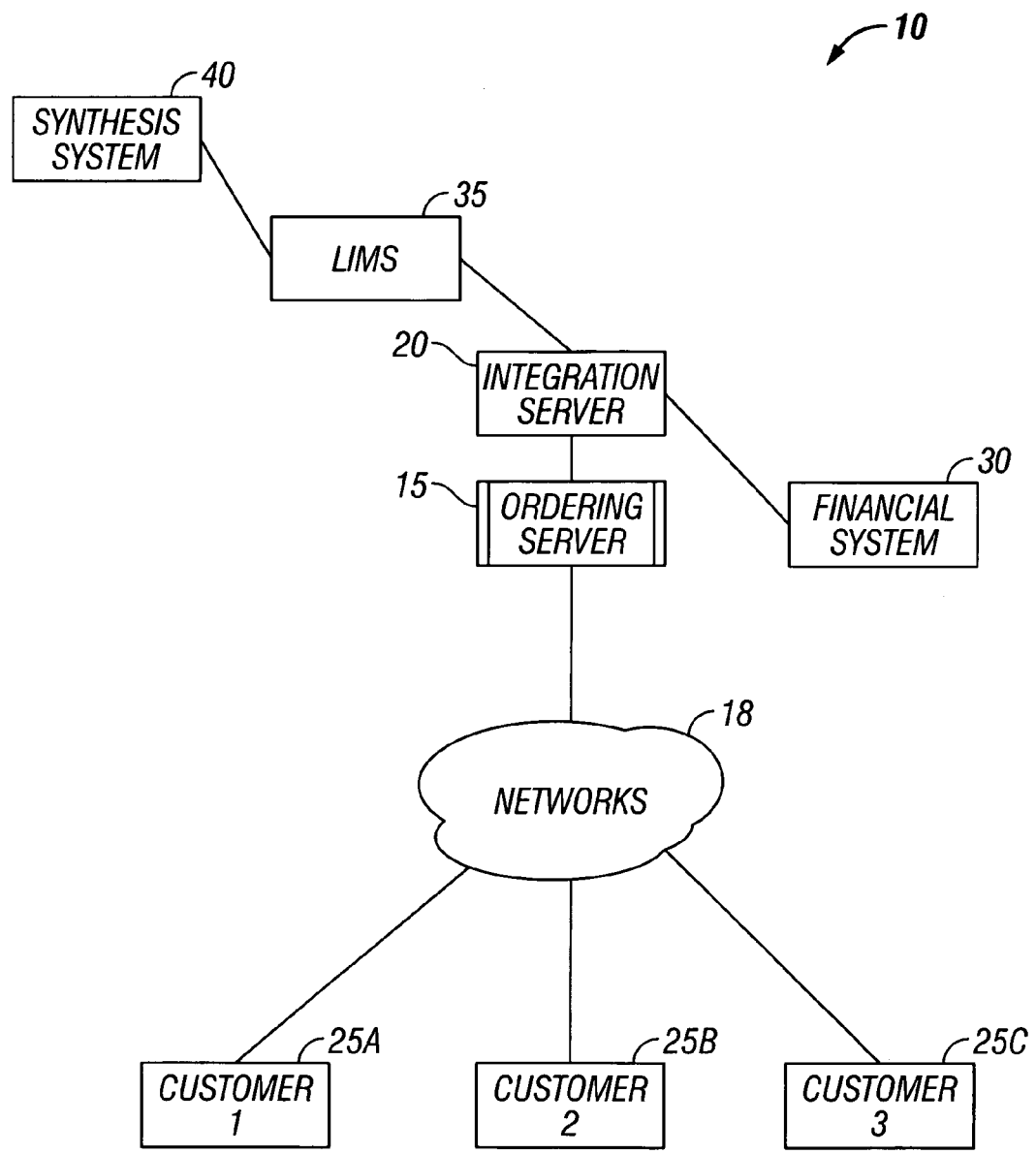
FIG. 1 is a schematic drawing of one embodiment of an oligonucleotide ordering system.

Embodiments of the invention relate to an on-line ordering system that allows a customer to order oligonucleotides through a computer network such as the Internet. In one embodiment, the system provides an enhanced validation engine which thoroughly scans a customer's order for errors. In this embodiment, a customer uploads a customer data file, such as a text file or an XML file, containing a list of oligonucleotides to a server. Once the file is uploaded, it can be scanned for a variety of errors. Errors can be identified according to configurable business rules and manufacturing parameters stored within the ordering system.

In order to provide a simplistic mechanism for the customer to know whether an error has occurred or not, embodiment of the system display graphical indicia of oligonucleotide containers which are color coded to indicate whether an error has occurred or not. For example, if the customer has ordered his oligonucleotides to arrive in three 96-well plates, then graphical indicia of these three containers will appear after the customer data file has been uploaded. In one embodiment, these container graphics will be color coded to indicate whether or not an error has occurred with any of the oligonucleotides that correspond to the container.

For example, if an error has occurred in one oligonucleotide of the second plate, then that plate may be colored red whereas the other two plates for which errors have not been identified may be colored green. Of course, the invention is not limited to any particular graphical indicia or, if color is the indicia used, any particular coloring scheme.

In one embodiment, if the customer selects the container graphic indicating an error by, for example, using a mouse or other input device, then an enhanced container graphic will be displayed. For example, if the container is a 96 well plate then each of the 96 wells of the microtiter plate can be shown as a dot. Within this enhanced container graphic, each individual well can be displayed as a dot. Each of the wells can be coded with error or pass indicia such as a color code that indicates which well contains an oligonucleotide with an error, and which well does not, respectively. For example, in one embodiment, the wells with oligonucleotides having an error will be indicated in red whereas the other dots will be indicated in green. If desired, an error or pass indicia or both can be associated with a text message that is displayed to the customer. A text error message can be useful to indicate the presence of an error as well as to advise a customer of possible solutions that will remove the error.

Additionally, the system may provide that when a customer moves the mouse cursor over any particular dot of a container graphic indicating an error, then a text or graphical display can appear in order to identify the type of error associated with the oligonucleotide at that position. Of course it should be realized that the invention is not limited to any particular shape of the containers or color schemes. For example, the container graphics might indicate a 384-well microtiter plate, an eppendorf tube, a falcon tube or any other well-known container designed to hold molecules such as oligonucleotides. Furthermore, error indicia can be accessed or selected by methods other than a mouse click such as a combination of keystrokes (often referred to in the art as a short-cut) or other methods known in the art for manipulating an image in a presentation layer or graphical customer interface.

An additional embodiment of the invention provides a system for conveniently ordering pools of oligonucleotides such that multiple different oligonucleotides are combined within a single container as part of the order. As will be explained more completely below, one embodiment of the invention provides a system wherein a container graphic indicating each container that has been ordered is displayed to the customer. The customer then selects a particular container from the container graphic to indicate the first container that holds one or more oligonucleotides to be part of the pooled mixture. In this embodiment, the customer then selects a second container graphic that holds the second oligonucleotide(s) that are to be admixed with the oligonucleotide(s) from the first selected container. The system then generates a list of the containers that are to be mixed together to create the proper pooled container of oligonucleotide mixtures. It should be realized that the system may display a variety of container graphics that allow the customer to choose which containers to mix into one or more pools. The system can further display parameters by which the containers should be mixed.

Definitions

Container

Container refers to any vessel or substrate designed to hold, store or transfer biologically active molecules such as oligonucleotides. Examples of containers include multiwell plates, eppendorf tubes and falcon tubes. A multiwell plate can include, for example, 8, 16, 96, 384, or 1536 wells.

Further examples of containers include a substrate having a surface to which one or more biologically active molecule is attached such as a bead or array. Arrays are populations of different molecules that are attached to one or more substrates such that the different molecules can be differentiated from each other according to relative location. Useful arrays include, without limitation, an array synthesized by photolithography-based polymer synthesis, such as an Affymetrix® GeneChip® and others known in the art (see, for example, U.S. patent application Ser. No. 09/536,841, International Publication No. WO 00/58516; U.S. Pat. Nos. 5,143,854, 5,242,974, 5,252,743, 5,324,633, 5,445,934, 5,744,305, 5,384,261, 5,405,783, 5,424,186, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, 6,136,269, 6,269,846, 6,022,963, 6,083,697, 6,291,183, 6,309,831 and 6,428,752; and in PCT Application Nos. PCT/US99/00730 (International Publication No. WO 99/36760) and PCT/US01/04285); a spotted array such as a CodeLink™ Array (Amersham Biosciences), an array manufactured using inkjet printing, such as a SurePrin™ array (Agilent Technologies); or a BeadChip™ Array (Illumina Inc.) or other bead based array such as those described in U.S. Pat. Nos. 6,023,540, 6,200,737, 6,327,410, 6,355,431 and 6,429,027; U.S. patent application publication No. US 2002/0102578 and PCT Publication Nos. WO 00/63437, WO 98/40726, and WO 98/50782.

Container Graphics

Container graphics refer to any pictorial representation of a container. The representation can be generated for display on a monitor, printout or a report. In one example, the representation can be rectangular and appear as an image of a microtiter plate or be circular and represent an eppendorf tube. Of course, the term container graphic is not limited to any particular shape. If desired a container graphic can include text or other characters. Alternatively, a container graphic can exclude such characters. Accordingly, a container graphic can include at least one pictorial representation that is not a text character.

Input Devices

The input device can be, for example, a keyboard, rollerball, mouse, voice recognition system or other device capable of transmitting information from a customer to a computer. The input device can also be a touch screen associated with the display, in which case the customer responds to prompts on the display by touching the screen. The customer may enter textual information through the input device such as the keyboard or the touch-screen. An input device can also be detector used to identify an item such as a bar code reader, RF tag reader or other tag reader.

Instructions

Instructions refer to computer-implemented steps for processing information in the system. Instructions can be implemented in software, firmware or hardware and include any type of programmed step undertaken by components of the system.

LAN

One example of the Local Area Network may be a corporate computing network, including access to the Internet, to which computers and computing devices comprising the system are connected. In one embodiment, the LAN conforms to the Transmission Control Protocol/Internet Protocol (TCP/IP) industry standard. In alternative embodiments, the LAN may conform to other network standards, including, but not limited to, the International Standards Organization's Open Systems Interconnection, IBM's SNA, Novell's Netware, and Banyan VINES.

Media

Media refers to images, sounds, video or any other multimedia type data that is entered into a system described herein.

For example, media can include a document that is entered into the system by a document scanner or transmitted over a network connection.

Microprocessor

The microprocessor may be any conventional general purpose single- or multi-chip microprocessor such as a Pentium® processor, a Pentium® Pro processor, a 8051 processor, a MIPS® processor, a Power PC® processor, or an ALPHA® processor. In addition, the microprocessor may be any conventional special purpose microprocessor such as a digital signal processor or a graphics processor. The microprocessor typically has conventional address lines, conventional data lines, and one or more conventional control lines.

Modules

The system is comprised of various modules as discussed in detail below. As can be appreciated by one of ordinary skill in the art, each of the modules can include various subroutines, procedures, definitional statements or macros, or a combination thereof. Each of the modules are typically separately compiled and linked into a single executable program. Therefore, the following description of each of the modules is used for convenience to describe the functionality of a particular system. Thus, the processes that are undergone by each of the modules may be arbitrarily redistributed to one of the other modules, combined together in a single module, or made available in, for example, a shareable dynamic link library.

Networks

The system may include any type of electronically connected group of computers including, for instance, the following networks: Internet, Intranet, Local Area Networks (LAN) or Wide Area Networks (WAN). In addition, the connectivity to the network may be, for example, remote modem, Ethernet (IEEE 802.3), Token Ring (IEEE 802.5), Fiber Distributed Datalink Interface (FDDI) or Asynchronous Transfer Mode (ATM). Note that computing devices may be desktop, server, portable, hand-held, set-top, or any other desired type of configuration. As used herein, an Internet includes network variations such as public internet, a private internet, a secure internet, a private network, a public network, a value-added network, an intranet, and the like.

Operating Systems

The system may be used in connection with various operating systems such as: UNIX, Disk Operating System (DOS), OS/2, or a Windows system such as Windows 3.X, Windows 95, Windows 98, Windows 2000, Windows 2003, Windows XP, and Windows NT.

Oligonucleotide

As used here, "Oligonucleotide" means a DNA fragment. The fragment may be any length having more than two nucleotides such as at least about 7, 10, 15, 25, 50, 75 or more nucleotides. Useful ranges include, without limitation from about 2-500 nucleotides, or from about 10-100 nucleotides or from 5-25 nucleotides or from about 20-70 nucleotides in length.

Programming Languages

The system may be written in any programming language such as C, C++, C# (C sharp), BASIC, Pascal, Java, Visual Basic and FORTRAN and ran under the well-known operating system. C, C++, BASIC, Pascal, Java, Visual Basic and FORTRAN are industry standard programming languages for which many commercial compilers can be used to create executable code.

Exemplary embodiments of useful systems and methods are set forth in further detail below. It should be understood that various modifications can be made without departing from the invention.

System Overview

FIG. 1 provides an overview of an oligonucleotide ordering system 10. The system includes an ordering server 15 that communicates with a network 18. The ordering server 15 may communicate with the network 18 through any well-known means, including high-speed digital data lines or wireless communication systems.

Communicating with the ordering server 15 is an integration server 20. The integration server 20 integrates data from a variety of sources to provide an enhanced oligonucleotide ordering system 10. As illustrated, the integration server 20 communicates with a financial system 30, and a laboratory information management system (LIMS) 35. As shown, the LIMS 35 communicates with a synthesis system 40. The financial system 30 may be any well-known financial system for managing a corporation, such as that provided by SAP®, Oracle®, PeopleSoft®, JD Edwards® or other well-known vendors. The laboratory information management system (LIMS) 35 may be any well-known system such as those offered by WildType® or PerkinElmer®. The synthesis system 40 can be a manufacturing environment for producing oligonucleotides. Many such systems exist, such as those housed at oligonucleotide synthesis companies such as Illumina Inc.®, or InVitrogen® or those housed at array manufacturers such as those described previously herein.

As shown in FIG. 1, a series of customers 25A, 25B and 25C communicate with a network 18 in order to access the ordering server 15 and place an oligonucleotide order. The customer computers 25A-C can be any well-known computer system that communicates through a network, such as the Internet. It will be understood that customers can be individuals or entities that access a system externally, for example, through the Internet or can be internal customers that access the system from a local network such as an Intranet.

Figure 2:
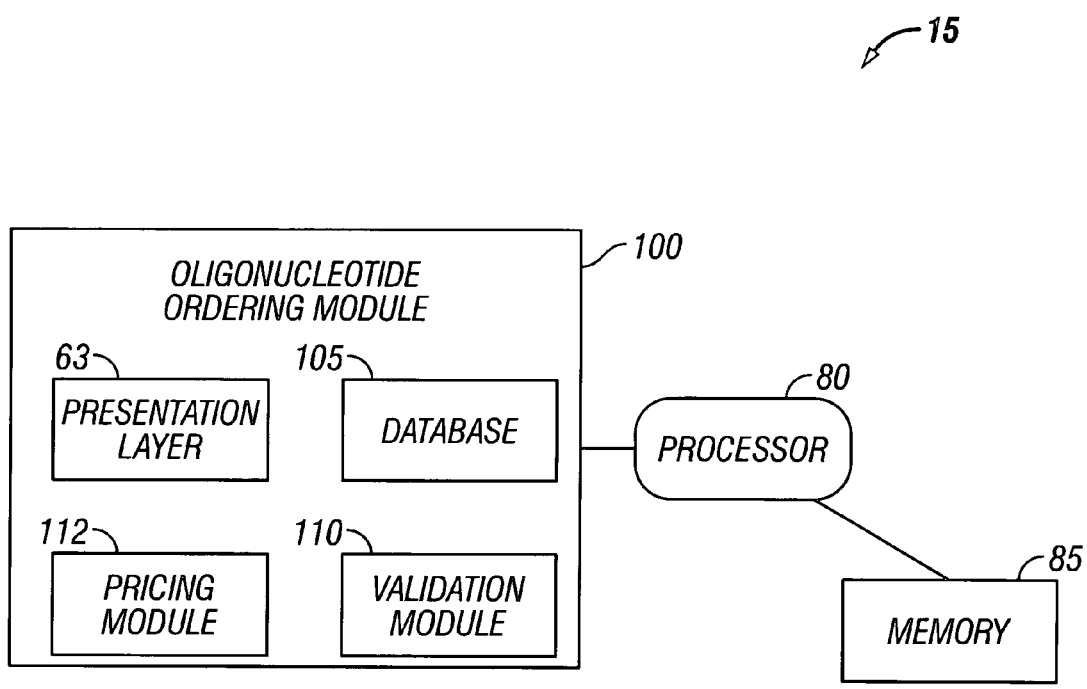
FIG. 2 is a schematic drawing of one embodiment of an ordering server within an oligonucleotide ordering system.

Referring now to FIG. 2, the ordering server 15 is explained in more detail. As shown, the ordering system 15 includes a processor 80 that connects to a memory 85. The ordering server 15 can include any well-known type of processor 80, such as those designed by Intel, AMD or Motorola. In addition, the memory 85 can be any type of conventional random access memory or read-only memory which interacts with the processor 80. Also within the ordering server 15 and linked to the processor 80 is an oligonucleotide ordering module 100 which manages the interface presented to the customer. The ordering module 100 includes a database 105, a validation module 110 and a pricing module 112. As will be explained below, the database 105 and validation module 110 are used to validate the oligonucleotide customer data file provided by each of the customers 25A-C. Also within the oligonucleotide ordering module 100 is a presentation layer 63 that is used to generate the container graphics that will be explained in more detail below.

Process Overview

Figure 3:
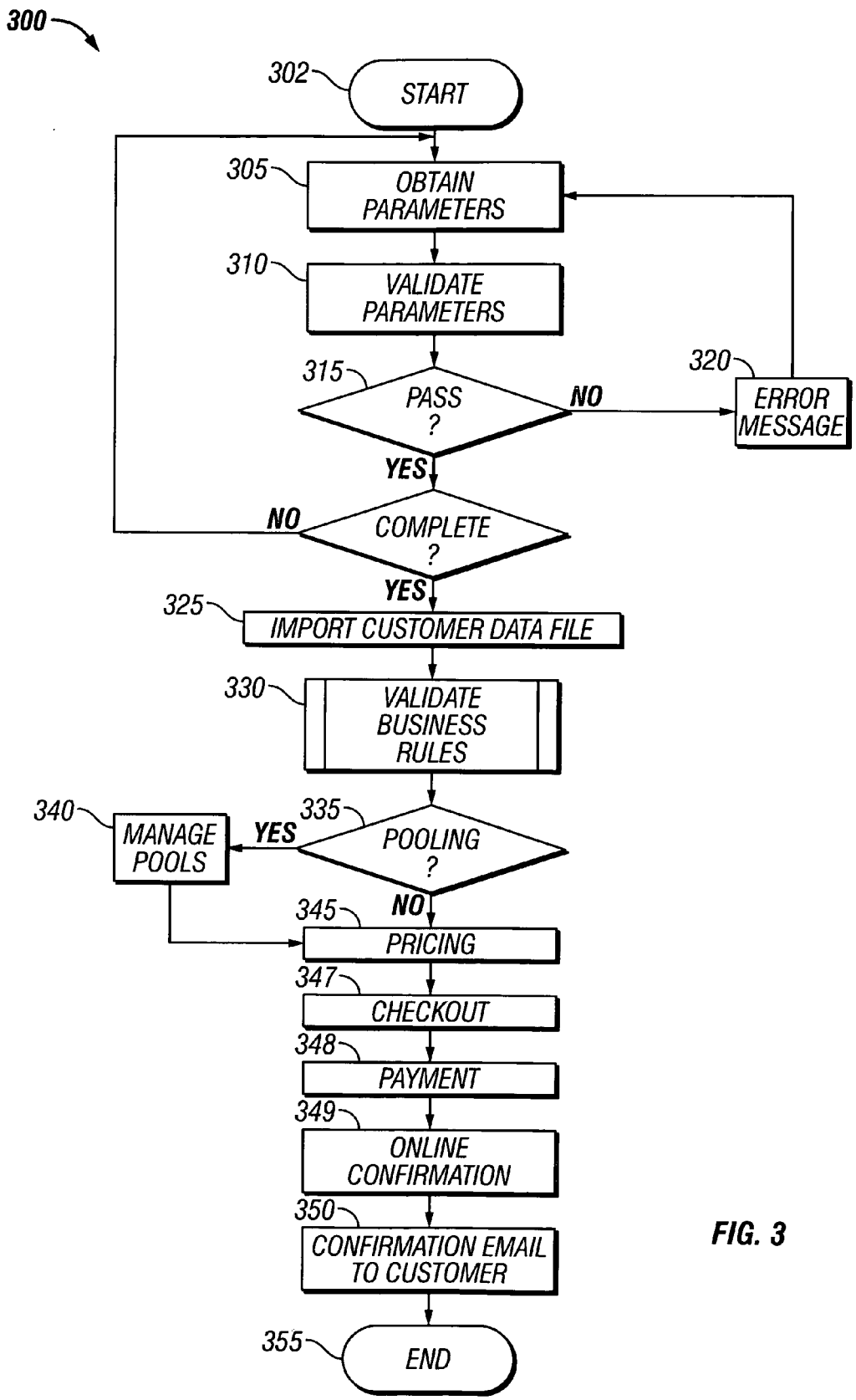
FIG. 3 is a process flow diagram illustrating an overview of one embodiment of a method for ordering oligonucleotides.

FIG. 3 provides one embodiment of a process 300 for ordering oligonucleotides through an on-line ordering system. The process 300 begins at a start state 302 and then moves to a state 305 where initial parameters regarding the order are received from the customer and stored to a database. The database for storing the parameters can be the database 105 or any other database within the system 10. These parameters might be, for example, the type of container desired by the customer, such as a microtiter plate or eppendorf tube. Other parameters might be whether the oligonucleotides should be delivered in solution, or dried. Other parameters include a synthesis scale, buffer type, normalization, volume and concentration. For example, validation can be carried out to determine that the normalized volume of solution and concentration of each oligonucleotide does not exceed predetermined levels for a selected optical density at 260 nm.

Once the initial parameters are obtained by the system from the customer at state 305, the process 300 moves to a state 310 wherein the parameters are validated to ensure that the order can proceed properly. For example, the system may ensure that the volume of solution ordered by the customer will fit into the type of containers also selected by the customer. Other types of validation include ensuring that the normalized volume of solution is sufficient to achieve the required concentration of each oligonucleotide and ensuring that the resulting concentration of oligonucleotide is sufficient to achieve a predetermined optical density at 260 nm which indicates the yield of DNA in the solution.

If the process 300 does not pass validation at the decision state 315, the process 300 moves to an error state 320 wherein the customer is provided with a message indicating the errors and the parameters being validated. The message can be, for example, an on-screen text message, new window, printout or e-mail message. The process 300 then returns to the state 305 in order to obtain corrected parameters.

Once the parameters have been validated at the state 310, the process 300 moves to a decision state 315 wherein a determination is made whether the initial parameters have passed the validation test. If the initial parameters pass the validation test, then the process 300 moves to a decision state 318 to determine whether the required parameters have been entered, and thus the order can be completed. If additional parameters are required, then the process 300 returns to the state 305 to obtain the additional parameters. If there are no more parameters required, the process 300 moves to state 325 wherein a customer data file containing the oligonucleotides is imported to the ordering server.

This importation process is normally achieved by uploading the customer data file to a storage in the server 15, through the network 18. The storage can include random access memory or a hard disk. The customer data file may include the list of oligonucleotides being ordered, including their DNA sequences, plus a variety of other useful parameters. As used herein, the term "oligonucleotide sequence data" refers to the nucleotide sequence of an oligonucleotide being ordered. These parameters might be, for example, the name, location, sequence, modification or comments associated with each oligonucleotide. One example of the format of a customer data file for a 96 well microtiter plate is shown below in Table 1.

TABLE 1

Example Customer Data File

| Label | Row | Col | Long Description | SEQ ID NO. | Sequence |
|---|---|---|---|---|---|
| I11_040422_02_F | A | 1 | 013379_F_IRAV01-03_A02_Il17rc | 1 | TGTGTCCGTGTGGTGGTC |
| I11_040422_01_F | A | 2 | 010310_F_IRAV01-03_B11_Oprs1 | 2 | ATGAGGAGCTGCAGTGGG |
| I11_040422_01_F | A | 3 | 013459_F_IRAV01-03_C02_Nr4a1 | 3 | TCCCTGGACGTTATCCGA |
| I11_040422_01_F | A | 4 | 013434_F_IRAV01-03_C14_BC003323 | 4 | CGTGTGTGGCTTCGTCTG |
| I11_040422_01_F | A | 5 | 012154_F_IRAV01-03_C21_Slc29a1 | 5 | CCCAGAATGTGTCCTCGG |
| I11_040422_01_F | A | 6 | 010320_F_IRAV01-03_D17_Scgf | 6 | CCCACCAGACTGGGACAC |
| I11_040422_01_F | A | 7 | 013079_F_IRAV01-03_E09_Slc25a11 | 7 | AAGTTCCTGTTTGGGGGC |
| I11_040422_01_F | A | 8 | 013099_F_IRAV01-03_E19_D19Ertd675e | 8 | CTGACTGCGACGGCTACA |
| I11_040422_01_F | A | 9 | 010996_F_IRAV01-03_H15_Fcgrt | 9 | CATCTACGGGGCTTCCCT |
| I11_040422_01_F | A | 10 | 013209_F_IRAV01-03_I19_Tcf11 | 10 | AAGCGCAGAGTCGTCACC |
| I11_040422_01_F | A | 11 | 010170_F_IRAV01-03_I22_Irak1 | 11 | TTCCTTGCTTGCCCTTTG |
| I11_040422_01_F | A | 12 | 010315_F_IRAV01-03_J15_Il13ra2 | 12 | TTGCAATGGAAACCTCCTG |
| I11_040422_01_F | B | 1 | 013549_F_IRAV01-03_K06_Slc25a10 | 13 | CTGCGCATGACTGGAATG |
| I11_040422_01_F | B | 2 | 011086_F_IRAV01-03_K08_E2f5 | 14 | TCCTGGATCTCAAAGCGG |
| I11_040422_01_F | B | 3 | 010215_F_IRAV01-03_K24_Crlf3 | 15 | TCCTTGGAGTGTTCCCCA |
| I11_040422_01_F | B | 4 | 013554_F_IRAV01-03_M10_Cklfsf3 | 16 | GGACTTCCTGCGCTGTGT |
| I11_040422_01_F | B | 5 | 011729_F_IRAV01-03_M17_Pla2g6 | 17 | AAGCCAGCGTTCATCCTG |
| I11_040422_01_F | B | 6 | 013559_F_IRAV01-03_M18_Abtb1 | 18 | CCTGGAGGCTAAGTGCGA |
| I11_040422_01_F | B | 7 | 013564_F_IRAV01-03_M22_Tnfaip1 | 19 | ACCCCTCGAGTCCCTGAC |
| I11_040422_01_F | B | 8 | 012554_F_IRAV01-03_N03_Bcap31 | 20 | TCCCATCCCTCTGTTGGA |
| I11_040422_01_F | B | 9 | 013369_F_IRAV01-03_O03_Araf | 21 | AGCAACGTGACCAGGAGC |
| I11_040422_01_F | B | 10 | 013364_F_IRAV01-03_O05_Nrbp | 22 | GGGGCACCAACACATGAT |

TABLE 1-continued

Example Customer Data File

| Label | Row | Col | Long Description | SEQ ID NO. | Sequence |
|---|---|---|---|---|---|
| Ill_040422_01_F | B | 11 | 013744_F_IRAV01-03_P13_Lass4 | 23 | TTGTGGTCGCCATCATTG |
| Ill_040422_01_F | B | 12 | 022456_F_IRAV55-58_A09_1500001K17Rik | 24 | ACAAGGCTAGGATGGGGC |
| Ill_040422_01_F | C | 1 | 023186_F_IRAV55-58_A17_2410002K23Rik | 25 | CCCGCTTCACTTTGCACT |
| Ill_040422_01_F | C | 2 | 023710_F_IRAV55-58_A21_Slc6a13 | 26 | CATGGTCGTTCTCCTGGG |
| Ill_040422_01_F | C | 3 | 024532_F_IRAV55-58_B04_5031409J19Rik | 27 | CCACTGTGGACCCCTCTG |
| Ill_040422_01_F | C | 4 | 024027_F_IRAV55-58_B05_Slc11a2 | 28 | GCATCGCGCTCTTTGTTT |
| Ill_040422_01_F | C | 5 | 024542_F_IRAV55-58_B10_C430015I23Rik | 29 | AGTCAACAGCGCAGCCTT |
| Ill_040422_01_F | C | 6 | 024072_F_IRAV55-58_B22_Fgf15 | 30 | GCCCAGAGAACAGCTCCA |
| Ill_040422_01_F | C | 7 | 020650_F_IRAV55-58_C12_Gnat1 | 31 | TTCTGTAGCCCTGCAGCC |
| Ill_040422_01_F | C | 8 | 039408_F_IRAV55-58_C18_Gng1 | 32 | AGCTTGTTCATGAGAGCTGG |
| Ill_040422_01_F | C | 9 | 023511_F_IRAV55-58_C20_Opn1sw | 33 | TAAGCAGTTCCGGGCTTG |
| Ill_040422_01_F | C | 10 | 024207_F_IRAV55-58_D10_Slc6a12 | 34 | AGAAGGGCCAGCTGGAGT |
| Ill_040422_01_F | C | 11 | 022751_F_IRAV55-58_E13_Foxj2 | 35 | AACTGCACAGGGAGACGC |
| Ill_040422_01_F | C | 12 | 023321_F_IRAV55-58_E14_Apob48r | 36 | AAGGAACTCCTGGGCCAC |
| Ill_040422_01_F | D | 1 | 023406_F_IRAV55-58_E16_Slco4a1 | 37 | CTCCCAGCGCTACGTTGT |
| Ill_040422_01_F | D | 2 | 022861_F_IRAV55-58_E23_Fbs1 | 38 | ACACGAACCCTGAGCTGC |
| Ill_040422_01_F | D | 3 | 023992_F_IRAV55-58_F13_Stc1 | 39 | ATCAAACGCACCTCCCAA |
| Ill_040422_01_F | D | 4 | 024667_F_IRAV55-58_F15_1110019O13Rik | 40 | ACCAAGGTGCAGAGTGGC |
| Ill_040422_01_F | D | 5 | 024147_F_IRAV55-58_F16_Ldlr | 41 | GGTTGCCCTCCTTGTCCT |
| Ill_040422_01_F | D | 6 | 023136_F_IRAV55-58_G05_Slc13a3 | 42 | AGTTTGCTGAACAGGCCG |
| Ill_040422_01_F | O | 7 | 023056_F_IRAV55-58_G13_Kcnj16 | 43 | TGCTCCACAAAGATGGCA |
| Ill_040422_01_F | D | 8 | 024937_F_IRAV55-58_G24_4930429H24Rik | 44 | TGCTGCACGAAGCAAGAC |
| Ill_040422_01_F | D | 9 | 024352_F_IRAV55-58_H01_Tmprss4 | 45 | CAGTGCTGCTGAGCCTGA |
| Ill_040422_01_F | D | 10 | 024807_F_IRAV55-58_H04_Slc26a1 | 46 | AGAATGTGGGACAGGCCA |
| Ill_040422_01_F | D | 11 | 035729_F_IRAV55-58_I14_Arf1 | 47 | TGAACCAGACCCCTCCCT |
| Ill_040422_02_F | D | 12 | 024287_F_IRAV55-58_I24_Ovol1 | 48 | CACCTCAAGGAACGCCAC |
| Ill_040422_01_F | E | 1 | 024442_F_IRAV55-58_J04_Slc16a4 | 49 | GGGGCTGCTACCTGGTTT |
| Ill_040422_01_F | E | 2 | 024232_F_IRAV55-58_J17_Trip4 | 50 | TCCTGCTTCCTGGTCGTC |
| Ill_040422_01_F | E | 3 | 024457_F_IRAV55-58_J24_AI648912 | 51 | ACAGCCTTCGTGTCCAGC |
| Ill_040422_01_F | E | 4 | 022596_F_IRAV55-58_K05_Slc27a4 | 52 | ATGCGGCCTGATGACATT |
| Ill_040422_01_F | E | 5 | 024292_F_IRAV55-58_K24_F2rl1 | 53 | GCCTCCTCCTTTGCATGA |
| Ill_040422_01_F | E | 6 | 024412_F_IRAV55-58_L09_Syap1 | 54 | CAGTCGGCCCAACTCACT |
| Ill_040422_01_F | E | 7 | 024917_F_IRAV55-58_M08_Mef2a | 55 | AGAGCCCTGATGCTGACG |
| Ill_040422_01_F | E | 8 | 023151_F_IRAV55-58_M11_Slc1Ba1 | 56 | TTGGGACTTCTGGTGGGA |
| Ill_040422_01_F | E | 9 | 023977_F_IRAV55-58_M12_Mtvr2 | 57 | TCTACAGCCAACGGAGCC |
| Ill_040422_01_F | E | 10 | 024707_F_IRAV55-58_N03_P2ry12 | 58 | TCCTGTTCTTTGCTGGGC |
| Ill_040422_01_F | E | 11 | 024907_F_IRAV55-58_N10_Hoxd9 | 59 | CCCCCAGTTTAGCGGACT |
| Ill_040422_01_F | E | 12 | 024057_F_IRAV55-58_N13_Tnfrsf11a | 60 | CCCTGGGCAGAAGTCAGA |

TABLE 1-continued

Example Customer Data File

| Label | Row | Col | Long Description | SEQ ID NO. | Sequence |
|---|---|---|---|---|---|
| Ill_040422_01_F | F | 1 | 024367_F_IRAV55-58_N15_Hmmr | 61 | ATATTGCTGCTCACGCCC |
| Ill_040422_01_F | F | 2 | 024377_F_IRAV55-58_N17_Asb6 | 62 | CATCAACAGGAGGGACCG |
| Ill_040422_01_F | F | 3 | 039682_F_IRAV55-58_N20_Taf13 | 63 | CCGTTCGTACTTCCCGAG |
| Ill_040422_01_F | F | 4 | 023965_F_IRAV55-58_P04_Scnn1g | 64 | CACTGGAGCCAAGGTGCT |
| Ill_040422_01_F | F | 5 | 025092_F_IRAV59-62_A02_Gcgr | 65 | GGCTGCTGAAGACACGGT |
| Ill_040422_01_F | F | 6 | 024557_F_IRAV59-62_A05_AA691260 | 66 | AGCTGGGCCTGCTTTTCT |
| Ill_040422_01_F | F | 7 | 026618_F_IRAV59-62_B06_Slc9a8 | 67 | CTCACAGGCCCTTGGCTA |
| Ill_040422_01_F | F | 8 | 026628_F_IRAV59-62_B10_Atrl1 | 68 | AAAGGGATGGAGCCTTGC |
| Ill_040422_01_F | F | 9 | 034194_F_IRAV59-62_C04_Kcnip1 | 69 | GACACTCCCAGGCAGCAT |
| Ill_040422_01_F | F | 10 | 026753_F_IRAV59-62_D04_Pdgfd | 70 | ACTGCTGATGCCCTGGAC |
| Ill_040422_01_F | F | 11 | 026828_F_IRAV59-62_D08_A930021G21Rik | 71 | CTGGCCCTCTGCTGTGAT |
| Ill_040422_01_F | F | 12 | 026371_F_IRAV59-62_D13_Gpnmb | 72 | AGGGGCAGATGATGGTGA |
| Ill_040422_01_F | G | 1 | 026356_F_IRAV59-62_D17_Wnt2 | 73 | GTACAATGGGGCCATCCA |
| Ill_040422_01_F | G | 2 | 026898_F_IRAV59-62_D20_Nfkbie | 74 | GGATGGAGACACGCTGCT |
| Ill_040422_01_F | G | 3 | 026893_F_IRAV59-62_D22_Synpr | 75 | AATCTGGGGCCAACTTCC |
| Ill_040422_01_F | G | 4 | 026001_F_IRAV59-62_E05_Gpr84 | 76 | TCCTCATTGCCCACCCTA |
| Ill_040422_01_F | G | 5 | 026768_F_IRAV59-62_F08_Cacnb4 | 77 | CTGGAGGCATACTGGCGT |
| Ill_040422_01_F | G | 6 | 026808_F_IRAV59-62_F16_Syt13 | 78 | GCCTCAAGAGGCAGGTCA |
| Ill_040422_01_F | G | 7 | 025626_F_IRAV59-62_G02_Chx10 | 79 | CGGTGTGGCGAGTTCTCT |
| Ill_040422_01_F | G | 8 | 026206_F_IRAV59-62_H07_Bmp4 | 80 | CCTGCAGCGATCCAGTCT |
| Ill_040422_01_F | G | 9 | 025601_F_IRAV59-62_I02_Cklfsf4 | 81 | CCTCGAGCACCTCCATGA |
| Ill_040422_01_F | G | 10 | 026573_F_IRAV59-62_J13_Hnf4 | 82 | CACAGCCATCACCACCAA |
| Ill_040422_01_F | G | 11 | 026903_F_IRAV59-62_J14_Slc12a8 | 83 | TGCTTGGTGCCGTCTGTA |
| Ill_040422_01_F | G | 12 | 026888_F_IRAV59-62_J16_Slc2a3 | 84 | AAGGAGACCCCTGGCAAC |
| Ill_040422_01_F | H | 1 | 038057_F_IRAV59-62_J21_Retnlb | 85 | GCAGCTGTTGCTTATCAAGG |
| Ill_040422_01_F | H | 2 | 025401_F_IRAV59-62_K22_Fgfr4 | 86 | TCCACGGGGAGAATCGTA |
| Ill_040422_01_F | H | 3 | 026503_F_IRAV59-62_L01_AW53B212 | 87 | TAAGGCTGGCCCAGAATG |
| Ill_040422_01_F | H | 4 | 026813_F_IRAV59-62_L20_Gng7 | 88 | CGCCCCTAGACCCTTGTT |
| Ill_040422_01_F | H | 5 | 026433_F_IRAV59-62_L21_Rai3 | 89 | TCTTGCCCGAGTTTCGAC |
| Ill_040422_01_F | H | 6 | 038172_F_IRAV59-62_L22_Sra1 | 90 | AGCTGTACGTGAAGCCCG |
| Ill_040422_01_F | H | 7 | 025811_F_12AV59-62_M11_siglecl1 | 91 | GAAAGAAGGATGCGGGGT |
| Ill_040422_01_F | H | 8 | 026673_F_IRAV59-62_N20_Kcne2 | 92 | TCGGCATGTTCTCGTTCA |
| Ill_040422_01_F | H | 9 | 025581_F_IRAV59-62_O15_Six1 | 93 | CTCGGTCCTTCTGCTCCA |
| Ill_040422_01_F | H | 10 | 026081_F_IRAV59-62_O21_Slc26a7 | 94 | GTTTTGATCATTGCCGCC |
| Ill_040422_01_F | H | 11 | 026386_F_IRAV59-62_P11_Syt13 | 95 | TCCCGACCCTGTTTTGAA |
| Ill_040422_01_F | H | 12 | 026663_F_IRAV59-62_P24_Slc4a10 | 96 | CTCAGGGAAAGGCGTTGA |

Once the customer data file has been imported into the system, the process 300 moves to a process state 330 wherein the customer data file is validated using values in database 105 (FIG. 2) and the business rules validation module 110 to determine whether the format of the customer data file is proper for continued processing within the system. This will be explained more completely with reference to FIG. 4 below.

Once a comparison has been achieved at the process state 330, the process 300 moves to a decision state 335 wherein a determination is made whether the customer wishes to pool individual oligonucleotide samples together to create a mixture of oligonucleotides. If the customer does wish to create a pool of oligonucleotides, the process 300 moves to a process state 340 wherein the customer can manage which pools are created from the individual oligonucleotide samples. This process of managing pools, and mixing individual oligonucleotide samples together, is explained more completely with reference to FIG. 7 below.

Once the process of managing pools has been completed at the process state 340, the process 300 moves to a process state 345 wherein the oligonucleotide pricing is managed by the system.

However, if a determination is made at the decision state 335 that the customer does not wish to pool any of the samples, the process 300 moves directly to the process state 345 in order to manage the pricing of the order. Pricing can be determined by a pricing engine that generates values based on, for example, specific components of the present order, customer order history such as earned discounts or rates pertaining to a particular customer or group of customers.

Once the process of managing pricing has been completed at the process state 345, the process 300 moves to a state 347 wherein the customer can checkout of the ordering process. At the state 347, an online shopping cart, for example, may be used to assist the customer in processing the order. This also allows the customer to store their order for a particular time period and then come back to complete the order at a later time.

Once the customer has initiated the checkout procedure, the process 300 moves to a payment state 348 wherein the system requests input as to the type of payment being made. Once payment has been arranged, the process 300 displays an online confirmation to the customer at a state 349. The process 300 then moves to a state 350 wherein a confirmation e-mail can be sent to the customer. The process then terminates at an end state 355.

Figure 4:
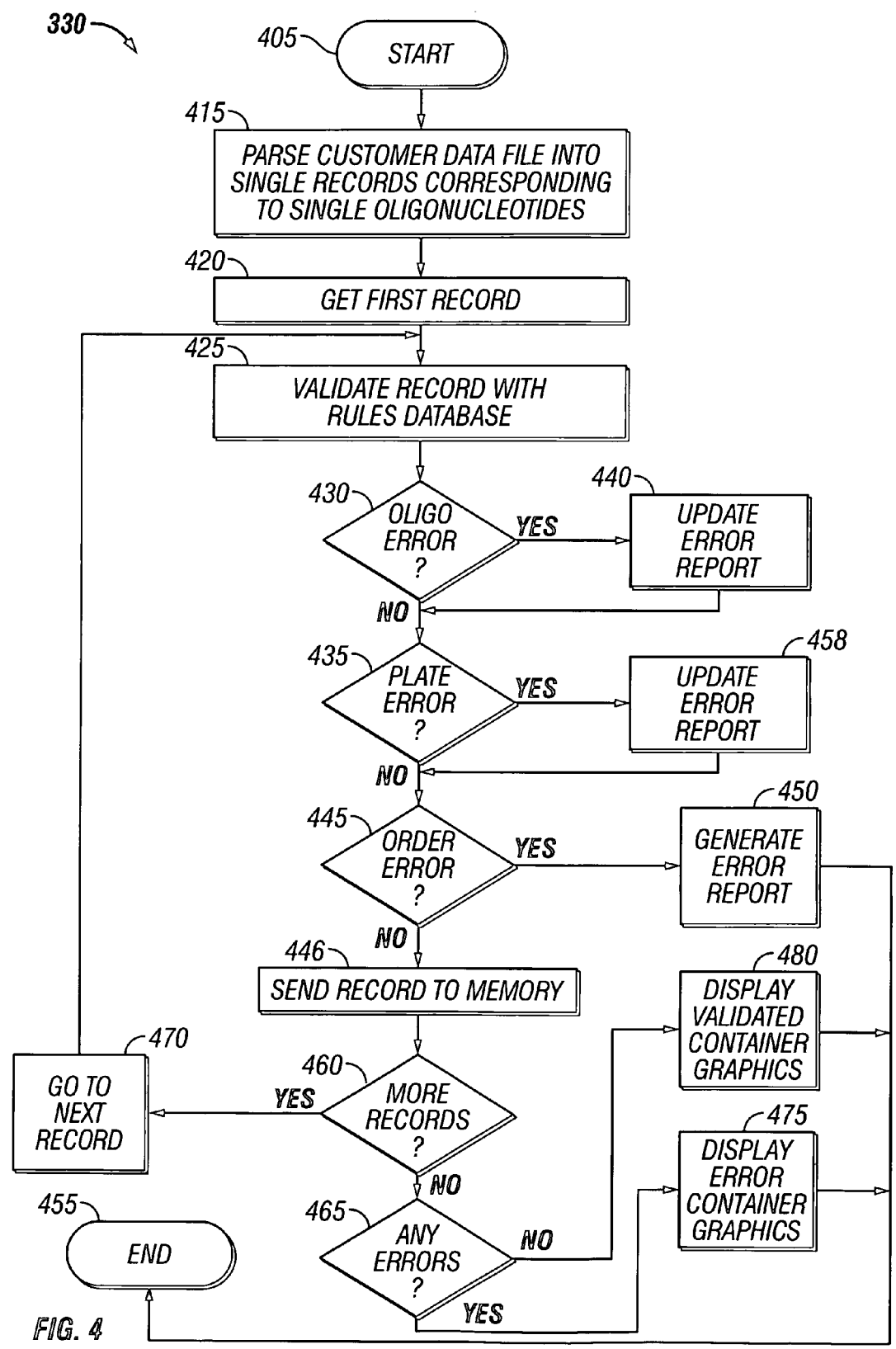
FIG. 4 is a process flow diagram illustrating one embodiment of a process for validating an oligonucleotide order.

Referring now to FIG. 4, an exemplary process 330 of comparing the imported customer data file to the business rules is explained more completely. The process 330 begins at a start state 405 and then moves to a state 415 wherein the customer data file is parsed into individual records wherein each record corresponds to a single oligonucleotide. This allows the process 330 to individually analyze each oligonucleotide that is being ordered from within the imported customer data file.

The process 330 then moves to a state 420 wherein the first record within the imported customer data file is identified. At state 425, the process 330 validates the first record of the imported customer data file using values in the rules database. During this validation, a number of checks are made concerning the oligonucleotide identified in the record, the parameters previously obtained at state 305 (FIG. 3), and the values stored within the rules database. Examples of such rules can be seen in Table 2 below.

TABLE 2

Examples of Rules in a Rules Database

| | |
|---|---|
| 1 | Accepted oligo lengths are 15 to 80 bases. |
| 2 | For unmodified oligos, the length difference between the longest and shortest oligo in a plate must be 30 bases or less. |
| 3 | An order containing oligos greater than 50 bases in length must select a starting synthesis scale of 50 nmol or higher. |
| 4 | Orders must contain a minimum average of 48 oligos per plate across the entire order. |
| 5 | Plate names must be unique for all plates within an order. |
| 6 | Plate names must be 15 characters or less in length. |
| 7 | Valid sequences can contain A, C, G, or T only. |
| 8 | Row and column designations within a plate must be unique. |
| 9 | Accepted row and column designations for a 96-well plate are A1 through H12. |
| 10 | Accepted row and column designations for a 384-well plate are A1 through P24. |
| 11 | Normalized volume must not exceed the working volume for the selected plate. |
| 12 | Normalized volume must be 10 µl or greater. |
| 13 | Normalized concentration must be greater than 1 and less than 200 uM. |
| 14 | Normalized volume and concentration must not exceed the guaranteed minimum ending OD yield at the selected synthesis scale. |
| 15 | Plate pooling is only available when concentration and volume normalization are selected. |
| 16 | Aliquoting is only available when concentration or volume normalization is selected. |
| 17 | Volume per aliquot must be 10 µl or greater. |
| 18 | Combined aliquot volume and concentration must not exceed the guaranteed minimum ending OD yield at the selected synthesis scale. |
| 19 | Pooled plate name must be 15 characters or less in length. |
| 20 | Pooled plate must contain 10 µl or greater volume from each source plate. |
| 21 | Each source plate can only be used in a single pooled plate. |

As demonstrated by the example of Table 2, a rule can require that the length of an oligonucleotide that is ordered be within a particular range. Thus, a rule can require a minimum length or maximum length for an oligo being ordered. A rule can specify the average length or range of lengths for a set of oligos. For example, a maximum length difference between the longest and shortest oligos in an order can be established by a rule. A rule can also require that particular synthesis conditions are used for oligonucleotides of a particular length. For example, a minimum synthesis scale can be required based on the length of one or more oligos being at or above a particular threshold value. The number of oligos ordered, in total or in one or more containers, can be specified by a rule. For example, a rule can specify that each plate in an order have a minimum number of oligonucleotides, or a minimum average number of oligonucleotides per plate can be specified across all or part of an order.

One or more rules can require that naming conventions are maintained such as the syntax of a container name, non-redundancy for the names of separate containers, location of wells in a container, or the like. General storage or synthesis conditions can be required to occur within particular limits according to rules. For example, one or more rules can specify minimum or maximum volume for a container, concentration of an oligo in a container, consistency between requested yield and requested reaction conditions (such as concentration and volume).

One or more rule can specify that particular criteria are satisfied for pooling such as the volume of sample to be transferred to a pooled container (i.e. the recipient container into which samples from donor plates are combined) is within a predefined range, the volume capacity for a pooled container is not exceeded, or the oligo mixture in a pooled late has a final yield in a particular range. One or more rules can specify naming conventions for a pooled plate as exemplified above for other containers.

Of course, it should be realized that Table 2 only provides exemplary rules, and that the system is flexible enough to validate the customer data file for a wide variety of errors. In addition, new rules can be added to the algorithm or new values can be added to the rules database at any time in order to enhance the validation process.

Once a comparison has been completed at the state 425, the process 330 moves to a decision state 430 to determine whether an oligonucleotide error was found within the first record. Examples of such errors include: an incorrect nucleotide within the sequence, invalid length, invalid name or invalid location.

If a determination is made that there were no oligonucleotide errors at the decision state 430, the process 330 moves to a decision state 435 to determine whether any plate errors occurred as a result of the identified record within the customer data file. Examples of plate errors include invalid well location, invalid oligonucleotide quantity or invalid combination of modifications.

However, if a determination is made that there was an oligonucleotide error at the decision state 430, then the process 330 updates an error report log at a state 440 in order to track the particular error within this record of the customer data file. The process 330 then returns to decision state 435 to determine whether a plate error has occurred.

If no plate error has occurred at the decision state 435, then a decision is made whether an order error has occurred at the decision state 445. An order error is an error regarding a complete order, which results in the process 330 generating an error report at a state 450 and then terminating at an end state 455. Examples of such order errors include invalid optical density (yield), invalid file format or invalid average oligonucleotide length.

However, it should be realized that if there was a plate error at the decision state 435, then the error report log is updated at a state 458 to identify the particular error on the identified record of the customer data file. The process then returns to state 445 to determine whether any order errors had been made.

If a determination is made at the decision state 445 that no order errors have occurred, then the process 330 moves to a state 446 wherein the selected record is sent to the memory 85 so that a cached set of records is built. Once the current record is stored to memory, a determination is made at a decision state 460 whether more records exist within the customer data file to analyze. If additional records do exist, then the system moves to the next record at a state 470 and then returns to the state 425 to compare the newly obtained record to the rules database.

If a determination is made that more records do not exist in the customer data file, then the process 330 determines whether any errors had been found during processing at a decision state 465. If a determination is made that any errors occurred, for example at decision states 430 or 435, then the process moves to a state 475 wherein a series of container graphics indicating an error are displayed to the customer. One example of such display can be found in FIG. 5. Once the container graphics indicating an error have been displayed to the customer, the process 330 terminates at an end state 455.

If however no errors were found during processing at the decision state 465, then the process 330 displays a series of container graphics showing that the imported customer data file was validated at a state 480. An example of such a display can be found in FIG. 6. After the container graphics indicating validated entry of the customer data file have been displayed at the state 480, the process 330 terminates at the end state 455.

Accordingly, process 330 provides a module configured to check the parameters entered by the customer, and also check the oligonucleotide sequence data for errors. Process 330 also provides a module that is configured to display a graphic representing the type of container indicated by the customer. As explained above, the graphic is displayed to the customer in a way that indicates whether the oligonucleotide sequence data within the customer data file had at least one error.

Figure 5A:
FIG. 5A is a screenshot of container graphics illustrating an invalid oligonucleotide order.

FIG. 5A shows a screen shot of a display screen showing container graphics which indicate both valid and invalid entries from the customer data file. As indicated, the screen shows microtiter plate graphics, which are one type of container graphic, having reference numerals 505A, B, C, D, E, F, G, H. As indicated, graphics 505A and B are shaded to indicate that an error has occurred within those plates, whereas graphics 505C, D, E, F, G and H are shown as white to indicate that no errors occurred within the oligonucleotides corresponding to those microtiter plates.

Figure 5B:
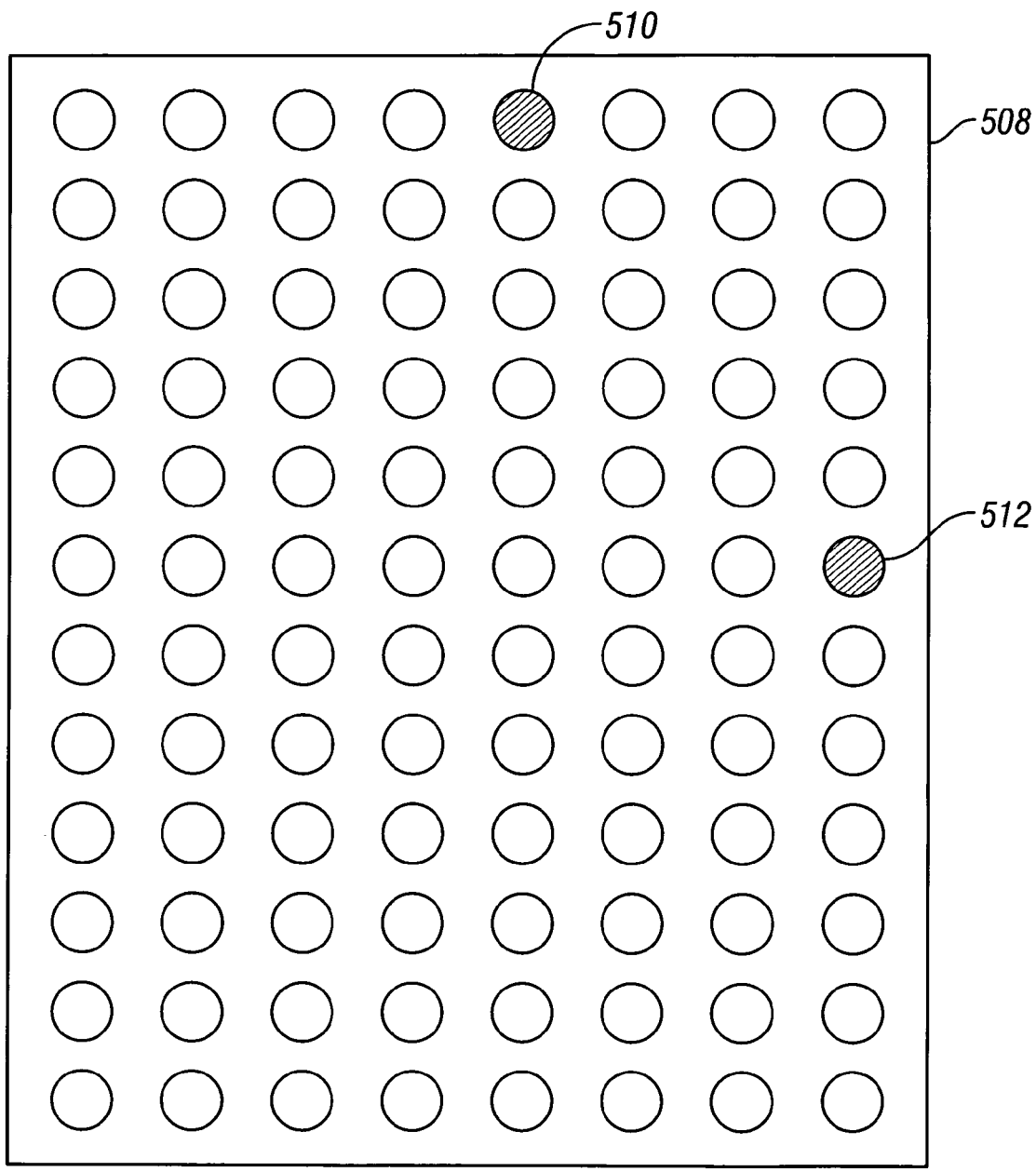
FIG. 5B is an expanded view of one container graphic from FIG. 5A that indicates invalid entries.

FIG. 5B shows a separate screen shot of microtiter plate 505B in a magnified view to indicate the display to the customer if that graphic is selected by a mouse click on the designated container. If the customer selects graphic 505B, then a graphic 508 is presented to the customer. As shown, the graphic 508 includes a series of rows and columns mimicking the look of a 96-well microtiter plate. Each well of the microtiter plate is indicated by a colored dot. However, it should be noted that a first well 510 and a second well 512 are represented to have errors by showing them in a different color than the other dots. This indicates to the customer that the oligonucleotide data corresponding to those positions of the microtiter plate have an error. Thus, the graphic 508 can be configured to display a first color if the oligonucleotide sequence data has no errors and a second color if the oligonucleotide sequence data has at least one error.

In one embodiment, if the customer moves the mouse pointer over the top of either indicia 510 or 512, then text will appear over the indicia indicating the error found with the oligonucleotide data associated with that position of the microtiter plate. Alternatively or additionally, a window can pop up with information indicating the error. This display mechanism, of showing the customer a graphical indicia of the container being ordered, such as a microtiter plate, and color coding that container to easily identify where errors have occurred, provides a convenient means for reporting errors to the customer. Furthermore, presentation of a text message provides the customer with guidance for correcting an error.

In one embodiment, the system is configured to allow a customer to send an error message to a printer or an e-mail message. Such a "send error message" option provides an advantage for communication regarding defects in a customer data file. This is particularly helpful for customers from larger organizations, in which an individual placing the order may not have sufficient technical knowledge to correct an error at the point of ordering and may wish to inform an appropriate individual of what errors have occurred.

Of course it should be realized that the graphical indicia shown on screen 500 can be in any format of a container for holding the oligonucleotides. It is not required that the containers be any particular graphic shape or color. In this embodiment of the invention, the container graphics are in the shape of a 96-well microtiter plate. However, container graphics of other types of microtiter plates and containers are within the scope of the invention. For example, the container graphics could be circular and represent tubes, where, for example, each circular graphic represents one eppendorf tube.

Figure 6:
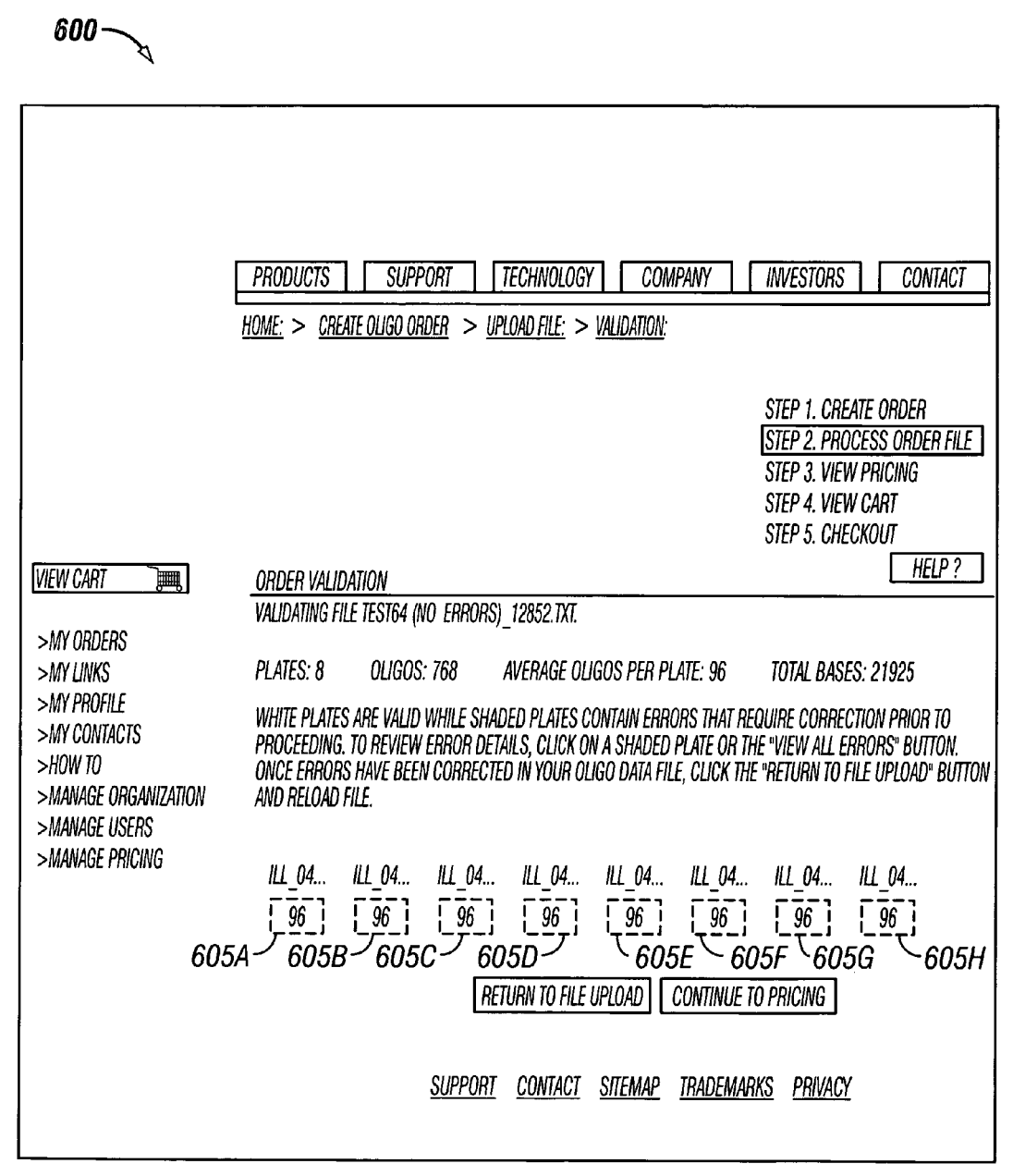

Referring to FIG. 6, a screenshot 600 of a valid oligonucleotide order is presented. In the screenshot 600 a series of container graphics 605A-F in the shape of a microtiter plate are shown. As indicated, each of the container graphics has the same color indicating that no errors occurred during processing of the customer data file. The customer is now assured that the oligonucleotide order can proceed from this state without any errors having been found in the order thus far.

Figure 7:
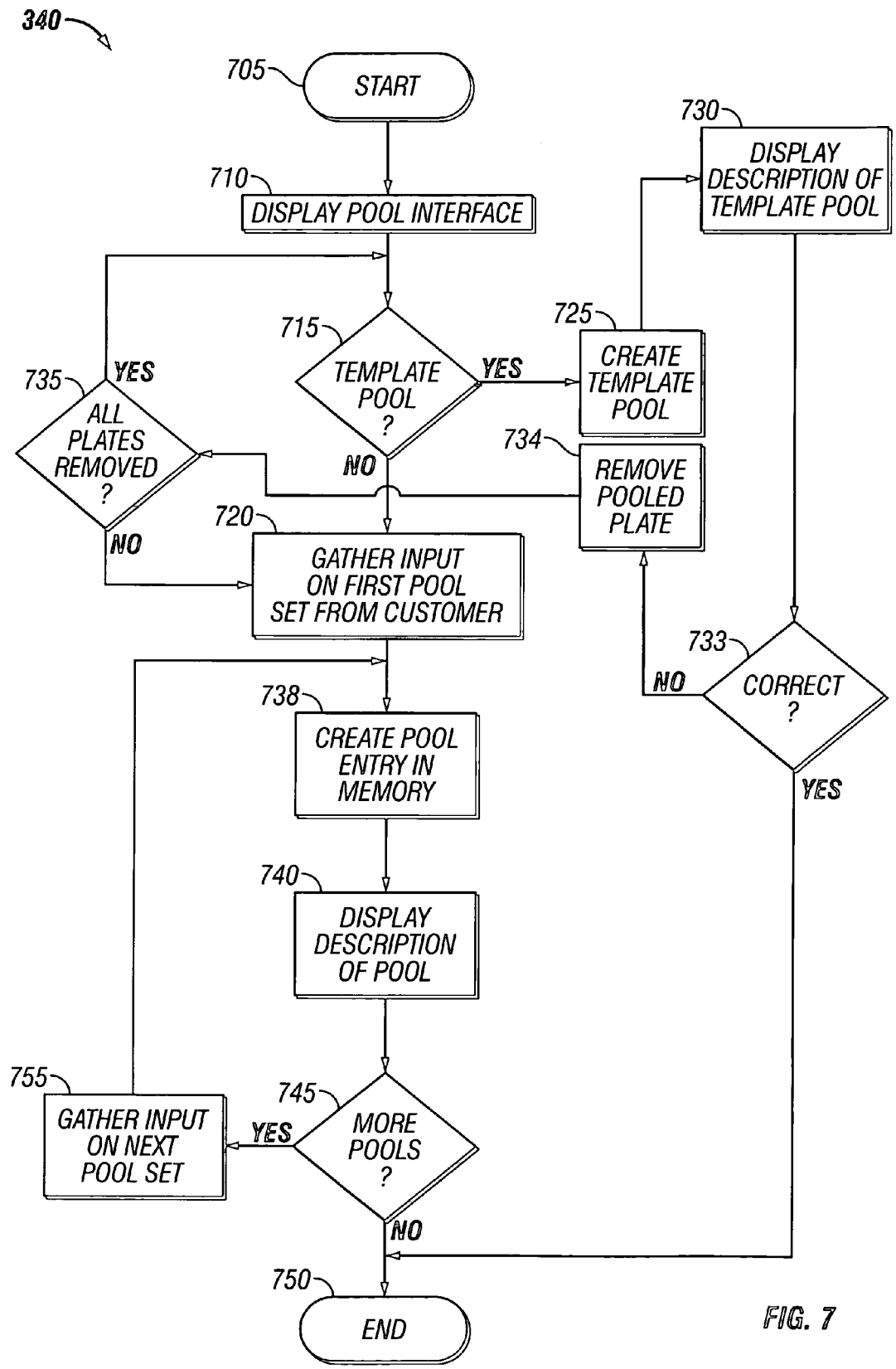
FIG. 7 is a process flow diagram illustrating one embodiment of a method for pooling multiple oligonucleotide containers.

Referring now to FIG. 7, an exemplary process 340 (FIG. 3) of managing pools of oligonucleotides is explained more completely. It should be realized that a pool of oligonucleotides is a mixture of different oligonucleotides taken from containers that have been ordered by the customer. As explained below, the system 10 is configured to present graphics representing a first container and a second container for holding oligonucleotides to the customer. The customer can then select the graphics which correspond to the containers he wishes to mix.

Figure 8:
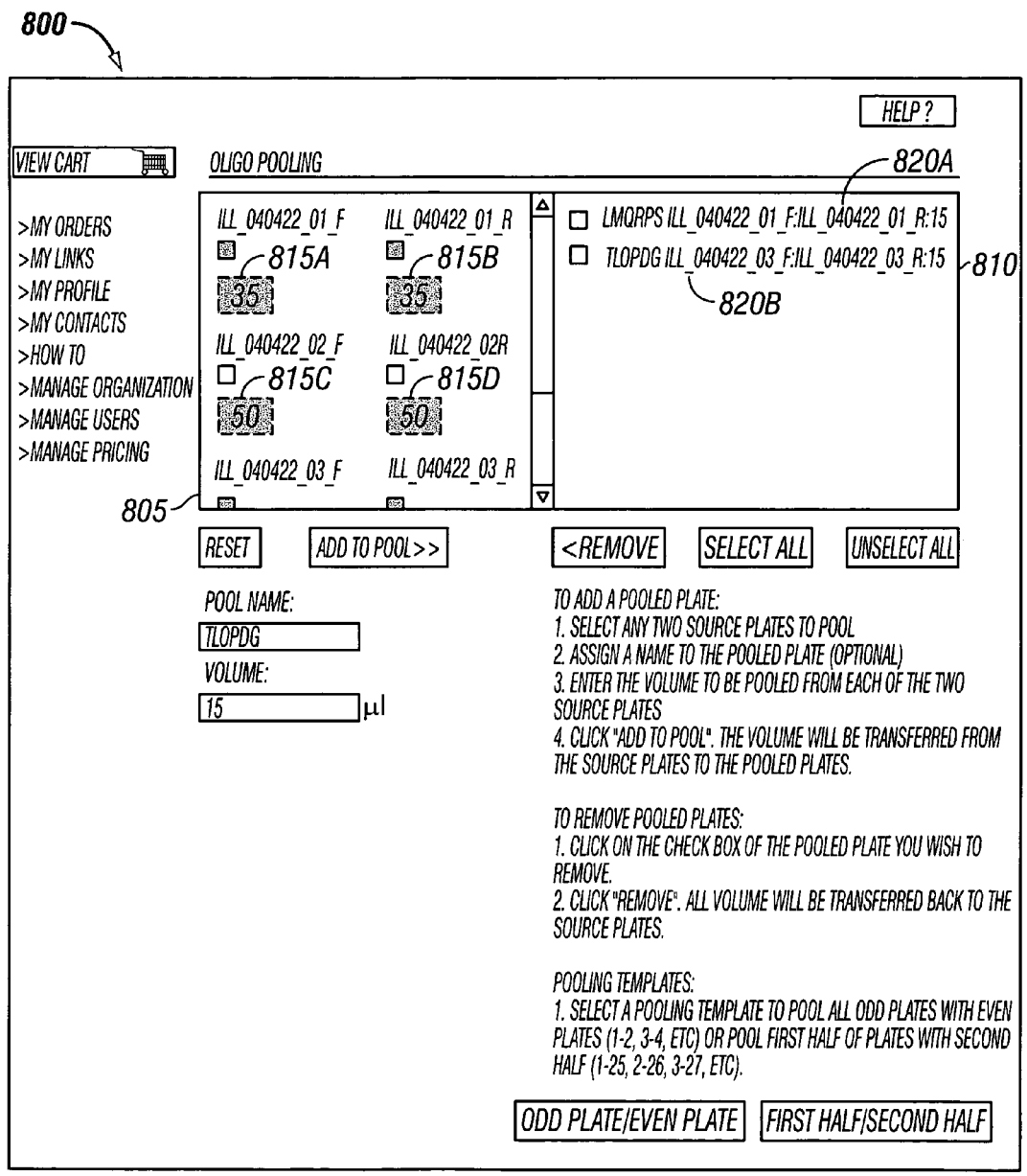
FIG. 8 is a screenshot of an interface to a method of pooling multiple oligonucleotide containers.

The process begins at a start state 705 and then moves to a state 710 wherein the pooling interface is displayed to the customer. One example of such an interface is provided in FIG. 8. A determination is then made at a decision state 715 whether or not to use a predefined template to aid in pooling samples. Such predefined templates can include, for example, automatic pooling of every other container in an order. Another type of predefined template would be automatic pooling of the first half of containers of an order with the second half of containers in an order. If a determination is made at state 715 that no template pooling will be done, the process 340 moves to a state 720 wherein input on the first pool set is gathered from the customer. As shown in FIG. 8, a series of graphics depicting the various containers that have already been ordered is presented to the customer. The customer then selects a first graphic that corresponds to the first container to be pooled. The customer then selects the second graphic that corresponds to a second container. After at least two containers have been selected in this manner, the customer indicates a choice by an input device such as a button or menu item to request for a pool to be made from the containers that have been selected through their corresponding graphics. Accordingly, the system is configured to present graphics representing a first selectable container and a second selectable container to the customer.

If a determination is made to use a template in order to pool samples together, then the process 340 moves to a state 725 wherein the template pool is created. After the template pool has been created by selecting the appropriate graphics, the process 340 moves to a state 730 where a description of the template pool is displayed to the customer.

A determination is then made at state 733 whether the correct template pools have been created. If a determination is made that the template pools were correct, then the process 340 terminates at state 750. However, if a determination is made that the pools were not created properly, the process 340 moves to a state 734 wherein the improper oligonucleotide pools are removed from the pool list. The process 340 then moves to a decision state 735 wherein a determination is made whether all of the plates that are being pooled have been removed from the list of possible pooled plates. If all of the plates have been removed, then the process 340 returns to the decision state 715 to begin the pooling process again.

If however, it is determined that not all plates have been removed, the process 340 moves to state 720 where input on the first pool set is gathered from the customer. Then the process 340 moves to a state 738 wherein a pool entry is created in memory from the input gathered at state 720. The process 340 then moves to a state 740 where a description of the pool entry is displayed to the customer. After displaying the pool entry description, a determination is made at state 745 whether more pools are desired. If it is determined at state 745 that more pools are desired, the process 340 moves to a state 755 where input on the next pool set is gathered. The process 340 then returns to state 735 where a pool entry is created from the input gathered at state 755. This pool entry is essentially a new order for a container that has a mixture of oligonucleotides from the selected containers. Accordingly, the system is configured to identify the containers corresponding to the graphics that were selected by the customer and thereafter create an order for a container comprising a mixture of oligonucleotides from the selected containers. If however, it is determined at state 745 that no further pools are desired, the process terminates at an end state 750.

Referring to FIG. 8, an exemplary screenshot 800 of the pooling interface is presented. Window 805 displays oligonucleotide containers 815A-D which a customer can select for pooling with a mouse click. Window 810 shows the description 740 (FIG. 7) of each pool entry 820A and 820B. Of course, it should be realized that the pool interface is not limited to what is shown in 800 but could be in any format for selecting oligonucleotide containers for pooling. Also, It is not required that the containers or descriptions be any particular graphic shape, or color.

INCORPORATION BY REFERENCE

All references cited herein, including patents, patent applications, papers, text books, and the like, and the references cited therein, to the extent that they are not already, are hereby incorporated herein by reference in their entirety.

Equivalents

The foregoing written specification is considered to be sufficient to enable one skilled in the art to practice the invention. The foregoing description and Examples detail certain preferred embodiments of the invention and describes the best mode contemplated by the inventors. It will be appreciated, however, that no matter how detailed the foregoing may appear in text, the invention may be practiced in many ways and the invention should be construed in accordance with the appended claims and any equivalents thereof.

What is claimed is:

1. A system for displaying a graphic indicating an error in an electronic order of oligonucleotides, comprising:
   - a database configured to receive a parameter defining a type of container for storing the oligonucleotides;
   - a server comprising a storage configured to receive a customer data file comprising oligonucleotide sequence data;
   - a first module configured to check said parameter and said oligonucleotide sequence data for errors; and
   - a second module configured to display a graphic representing said type of container, wherein said graphic indicates whether said oligonucleotide sequence data has at least one error.

2. The system of claim 1, wherein said container is a microtiter plate and said graphic is a graphical representation of a microtiter plate.

3. The system of claim 2, wherein said graphic is selectable, and upon such selection a second graphic of a microtiter plate is displayed.

4. The system of claim 3, wherein said second graphic comprises indicia that indicate the location of oligonucleotide data having at least one error.

5. The system of claim 4, wherein said second graphic comprises dots representing the positions of wells on said microtiter plate, and said indicia are colored dots.

6. The system of claim 1, wherein said container is a tube, and said indicia is a graphical representation of a tube.

7. The system of claim 1, wherein said storage is a random access memory or a hard disk.

8. The system of claim 1, wherein said second module is configured to display a first color if said oligonucleotide sequence data has no errors and a second color if said oligonucleotide sequence data has at least one error.

9. A method in a specifically programmed computer for displaying a graphic indicating an error in an order of oligonucleotides, comprising:
   - receiving a parameter defining a type of container for storing oligonucleotides;
   - storing a customer data file comprising oligonucleotide sequence data;
   - verifying said parameter and said oligonucleotide sequence data for errors; and
   - displaying a graphic representing said type of container on a display, wherein said displayed graphic indicates whether said oligonueleotide sequence data has at least one error.

10. The method of claim 9, wherein said container is a microtiter plate and said graphic is a graphical representation of a microtiter plate.

11. The method of claim 10, wherein said graphic is selectable, and upon such selection a second graphic of a microtiter plate is displayed.

12. The method of claim 11, wherein said second graphic comprises indicia that indicate the location of oligonueleotide data having at least one error.

13. The method of claim 12, wherein said second graphic comprises dots representing the positions of wells on said microtiter plate, and said indicia are colored dots.

14. The method of claim 9, wherein said container is a tube, and said indicia is a graphical representation of a tube.

15. The method of claim 9, wherein said storage is a random access memory or a hard disk.

16. The method of claim 9, wherein displaying a graphic comprises displaying a first color if said oligonucleotide sequence data has no errors and a second color if said oligonucleotide sequence data has at least one error.

17. A computer storage media comprising instructions that when executed perform a method comprising:
   - receiving a parameter defining a type of container for storing oligonuelcolides;
   - storing a customer data file comprising oligonucleotide sequence data;
   - verifying said parameter and said oligonucleotide sequence data for errors; and
   - displaying a graphic representing said type of container on a display, wherein said displayed graphic indicates whether said oligonucleotide sequence data has at least one error.

* * * * *

UNITED STATES PATENT AND TRADEMARK OFFICE
CERTIFICATE OF CORRECTION

| | | |
|---|---|---|
| PATENT NO. | : 7,647,186 B2 | Page 1 of 1 |
| APPLICATION NO. | : 11/184215 | |
| DATED | : January 12, 2010 | |
| INVENTOR(S) | : Fowler et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1160 days.

Signed and Sealed this

Sixteenth Day of November, 2010

David J. Kappos
*Director of the United States Patent and Trademark Office*

SEQUENCE LISTING

```
<160> NUMBER OF SEQ ID NOS: 96

<210> SEQ ID NO 1
<211> LENGTH: 18
```

-continued

```
<212> TYPE: DNA
<213> ORGANISM: Artificial Sequence
<220> FEATURE:
<223> OTHER INFORMATION: Synthetically prepared nucleic acid sequence

<400> SEQUENCE: 1
tgtgtccgtg tggtggtc                                                 18

<210> SEQ ID NO 2
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 2
atgaggagct gcagtggg                                                 18

<210> SEQ ID NO 3
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 3
tccctggacg ttatccga                                                 18

<210> SEQ ID NO 4
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 4
cgtgtgtggc ttcgtctg                                                 18

<210> SEQ ID NO 5
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 5
cccagaatgt gtcctcgg                                                 18

<210> SEQ ID NO 6
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 6
cccaccagac tgggacac                                                 18

<210> SEQ ID NO 7
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 7
aagttcctgt ttgggggc                                                 18
```

```
<210> SEQ ID NO 8
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 8
ctgactgcga cggctaca                                                 18

<210> SEQ ID NO 9
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 9
catctacggg gcttccct                                                 18

<210> SEQ ID NO 10
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 10
aagcgcagag tcgtcacc                                                 18

<210> SEQ ID NO 11
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 11
ttccttgctt gccctttg                                                 18

<210> SEQ ID NO 12
<211> LENGTH: 19
<212> TYPE: DNA
<213> ORGANISM: Artificial Sequence
<220> FEATURE:
<223> OTHER INFORMATION: Synthetically prepared nucleic acid sequence

<400> SEQUENCE: 12
ttgcaatgga aacctcctg                                                19

<210> SEQ ID NO 13
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 13
ctgcgcatga ctggaatg                                                 18

<210> SEQ ID NO 14
<211> LENGTH: 18
<212> TYPE: DNA
<213> ORGANISM: Artificial Sequence
<220> FEATURE:
<223> OTHER INFORMATION: Synthetically prepared nucleic acid sequence
```

```
<400> SEQUENCE: 14
tcctggatct caaagcgg                                                18

<210> SEQ ID NO 15
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 15
tccttggagt gttcccca                                                18

<210> SEQ ID NO 16
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 16
ggacttcctg cgctgtgt                                                18

<210> SEQ ID NO 17
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 17
aagccagcgt tcatcctg                                                18

<210> SEQ ID NO 18
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 18
cctggaggct aagtgcga                                                18

<210> SEQ ID NO 19
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 19
acccctcgag tccctgac                                                18

<210> SEQ ID NO 20
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 20
tcccatccct ctgttgga                                                18

<210> SEQ ID NO 21
<211> LENGTH: 18
```

```
<212> TYPE: DNA
<213> ORGANISM: Artificial Sequence
<220> FEATURE:
<223> OTHER INFORMATION: Synthetically prepared nucleic acid sequence

<400> SEQUENCE: 21
agcaacgtga ccaggagc                                                  18

<210> SEQ ID NO 22
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 22
ggggcaccaa cacatgat                                                  18

<210> SEQ ID NO 23
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 23
ttgtggtcgc catcattg                                                  18

<210> SEQ ID NO 24
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 24
acaaggctag gatggggc                                                  18

<210> SEQ ID NO 25
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 25
cccgcttcac tttgcact                                                  18

<210> SEQ ID NO 26
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 26
catggtcgtt ctcctggg                                                  18

<210> SEQ ID NO 27
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 27
ccactgtgga cccctctg                                                  18
```

```
<210> SEQ ID NO 28
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 28
gcatcgcgct ctttgttt                                                    18

<210> SEQ ID NO 29
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 29
agtcaacagc gcagcctt                                                    18

<210> SEQ ID NO 30
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 30
gcccagagaa cagctcca                                                    18

<210> SEQ ID NO 31
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 31
ttctgtagcc ctgcagcc                                                    18

<210> SEQ ID NO 32
<211> LENGTH: 20
<212> TYPE: DNA
<213> ORGANISM: Artificial Sequence
<220> FEATURE:
<223> OTHER INFORMATION: Synthetically prepared nucleic acid sequence

<400> SEQUENCE: 32
agcttgttca tgagagctgg                                                  20

<210> SEQ ID NO 33
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 33
taagcagttc cgggcttg                                                    18

<210> SEQ ID NO 34
<211> LENGTH: 18
<212> TYPE: DNA
<213> ORGANISM: Artificial Sequence
<220> FEATURE:
<223> OTHER INFORMATION: Synthetically prepared nucleic acid sequence
```

<400> SEQUENCE: 34
agaagggcca gctggagt                                                          18

<210> SEQ ID NO 35
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 35
aactgcacag ggagacgc                                                          18

<210> SEQ ID NO 36
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 36
aaggaactcc tgggccac                                                          18

<210> SEQ ID NO 37
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 37
ctcccagcgc tacgttgt                                                          18

<210> SEQ ID NO 38
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 38
acacgaaccc tgagctgc                                                          18

<210> SEQ ID NO 39
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 39
atcaaacgca cctcccaa                                                          18

<210> SEQ ID NO 40
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 40
accaaggtgc agagtggc                                                          18

<210> SEQ ID NO 41
<211> LENGTH: 18

-continued

```
<212> TYPE: DNA
<213> ORGANISM: Artificial Sequence
<220> FEATURE:
<223> OTHER INFORMATION: Synthetically prepared nucleic acid sequence

<400> SEQUENCE: 41
ggttgccctc cttgtcct                                                 18

<210> SEQ ID NO 42
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 42
agtttgctga acaggccg                                                 18

<210> SEQ ID NO 43
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 43
tgctccacaa agatggca                                                 18

<210> SEQ ID NO 44
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 44
tgctgcacga agcaagac                                                 18

<210> SEQ ID NO 45
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 45
cagtgctgct gagcctga                                                 18

<210> SEQ ID NO 46
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 46
agaatgtggg acaggcca                                                 18

<210> SEQ ID NO 47
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 47
tgaaccagac ccctccct                                                 18
```

```
<210> SEQ ID NO 48
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 48
cacctcaagg aacgccac                                                 18

<210> SEQ ID NO 49
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 49
ggggctgcta cctggttt                                                 18

<210> SEQ ID NO 50
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 50
tcctgcttcc tggtcgtc                                                 18

<210> SEQ ID NO 51
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 51
acagccttcg tgtccagc                                                 18

<210> SEQ ID NO 52
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 52
atgcggcctg atgacatt                                                 18

<210> SEQ ID NO 53
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 53
gcctcctcct ttgcatga                                                 18

<210> SEQ ID NO 54
<211> LENGTH: 18
<212> TYPE: DNA
<213> ORGANISM: Artificial Sequence
<220> FEATURE:
<223> OTHER INFORMATION: Synthetically prepared nucleic acid sequence
```

```
<400> SEQUENCE: 54
cagtcggccc aactcact                                                    18

<210> SEQ ID NO 55
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 55
agagccctga tgctgacg                                                    18

<210> SEQ ID NO 56
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 56
ttgggacttc tggtggga                                                    18

<210> SEQ ID NO 57
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 57
tctacagcca acggagcc                                                    18

<210> SEQ ID NO 58
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 58
tcctgttctt tgctgggc                                                    18

<210> SEQ ID NO 59
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 59
cccccagttt agcggact                                                    18

<210> SEQ ID NO 60
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 60
ccctgggcag aagtcaga                                                    18

<210> SEQ ID NO 61
<211> LENGTH: 18
```

```
<212> TYPE: DNA
<213> ORGANISM: Artificial Sequence
<220> FEATURE:
<223> OTHER INFORMATION: Synthetically prepared nucleic acid sequence

<400> SEQUENCE: 61
atattgctgc tcacgccc                                                  18

<210> SEQ ID NO 62
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 62
catcaacagg agggaccg                                                  18

<210> SEQ ID NO 63
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 63
ccgttcgtac ttccccgag                                                 18

<210> SEQ ID NO 64
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 64
cactggagcc aaggtgct                                                  18

<210> SEQ ID NO 65
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 65
ggctgctgaa gacacggt                                                  18

<210> SEQ ID NO 66
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 66
agctgggcct gcttttct                                                  18

<210> SEQ ID NO 67
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 67
ctcacaggcc cttggcta                                                  18
```

<210> SEQ ID NO 68
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 68
aaagggatgg agccttgc                                                 18

<210> SEQ ID NO 69
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 69
gacactccca ggcagcat                                                 18

<210> SEQ ID NO 70
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 70
actgctgatg ccctggac                                                 18

<210> SEQ ID NO 71
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 71
ctggccctct gctgtgat                                                 18

<210> SEQ ID NO 72
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 72
aggggcagat gatggtga                                                 18

<210> SEQ ID NO 73
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 73
gtacaatggg gccatcca                                                 18

<210> SEQ ID NO 74
<211> LENGTH: 18
<212> TYPE: DNA
<213> ORGANISM: Artificial Sequence
<220> FEATURE:
<223> OTHER INFORMATION: Synthetically prepared nucleic acid sequence

```
<400> SEQUENCE: 74
ggatggagac acgctgct                                              18

<210> SEQ ID NO 75
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 75
aatctggggc caacttcc                                              18

<210> SEQ ID NO 76
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 76
tcctcattgc ccaccta                                               18

<210> SEQ ID NO 77
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 77
ctggaggcat actggcgt                                              18

<210> SEQ ID NO 78
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 78
gcctcaagag gcaggtca                                              18

<210> SEQ ID NO 79
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 79
cggtgtggcg agttctct                                              18

<210> SEQ ID NO 80
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 80
cctgcagcga tccagtct                                              18

<210> SEQ ID NO 81
<211> LENGTH: 18
```

```
<212> TYPE: DNA
<213> ORGANISM: Artificial Sequence
<220> FEATURE:
<223> OTHER INFORMATION: Synthetically prepared nucleic acid sequence

<400> SEQUENCE: 81
cctcgagcac ctccatga                                                 18

<210> SEQ ID NO 82
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 82
cacagccatc accaccaa                                                 18

<210> SEQ ID NO 83
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 83
tgcttggtgc cgtctgta                                                 18

<210> SEQ ID NO 84
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 84
aaggagaccc ctggcaac                                                 18

<210> SEQ ID NO 85
<211> LENGTH: 20
<212> TYPE: DNA
<213> ORGANISM: Artificial Sequence
<220> FEATURE:
<223> OTHER INFORMATION: Synthetically prepared nucleic acid sequence

<400> SEQUENCE: 85
gcagctgttg cttatcaagg                                               20

<210> SEQ ID NO 86
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 86
tccacgggga gaatcgta                                                 18

<210> SEQ ID NO 87
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 87
taaggctggc ccagaatg                                                 18
```

```
<210> SEQ ID NO 88
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 88
cgcccctaga cccttgtt                                                 18

<210> SEQ ID NO 89
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 89
tcttgcccga gtttcgac                                                 18

<210> SEQ ID NO 90
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 90
agctgtacgt gaagcccg                                                 18

<210> SEQ ID NO 91
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 91
gaaagaagga tgcggggt                                                 18

<210> SEQ ID NO 92
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 92
tcggcatgtt ctcgttca                                                 18

<210> SEQ ID NO 93
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 93
ctcggtcctt ctgctcca                                                 18

<210> SEQ ID NO 94
<211> LENGTH: 18
<212> TYPE: DNA
<213> ORGANISM: Artificial Sequence
<220> FEATURE:
<223> OTHER INFORMATION: Synthetically prepared nucleic acid sequence
```

```
<400> SEQUENCE: 94
gttttgatca ttgccgcc                                                   18

<210> SEQ ID NO 95
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 95
tcccgaccct gttttgaa                                                   18

<210> SEQ ID NO 96
<211> LENGTH: 18
<212> TYPE: DNA
<213> ORGANISM: Artificial Sequence
<220> FEATURE:
<223> OTHER INFORMATION: Synthetically prepared nucleic acid sequence

<400> SEQUENCE: 96
ctcagggaaa ggcgttga                                                   18
```